United States Patent

Su et al.

Patent Number: 5,191,143
Date of Patent: Mar. 2, 1993

[54] PREPARATION OF ISOBUTYLENE

[75] Inventors: Wei-Yang Su, Austin; William A. Smith; Roya Tooloian, both of Houston, all of Tex.

[73] Assignee: Texaco Chemical Company, White Plains, N.Y.

[21] Appl. No.: 818,931

[22] Filed: Jan. 10, 1992

[51] Int. Cl.$^5$ .......................... C07C 1/00; C07C 7/00; C07C 7/17

[52] U.S. Cl. .................................. 585/640; 585/824; 585/852; 585/858; 585/859

[58] Field of Search ............... 585/640, 824, 852, 858, 585/859

[56] References Cited

U.S. PATENT DOCUMENTS 3,665,048   5/1972   Grane et al. ..................... 585/640
3,758,610   9/1973   Turner ............................. 585/640
4,165,343   8/1979   Levine et al. ..................... 585/638
4,529,827   7/1985   Drake .............................. 585/640

Primary Examiner—Anthony McFarlane
Assistant Examiner—Nhat D. Phan
Attorney, Agent, or Firm—Jack H. Park; Kenneth R. Priem; Carl G. Ries

[57] ABSTRACT

A method for the preparation of isobutylene substantially free from tertiary butyl formate and peroxides from a tertiary butyl alcohol feedstock contaminated with tertiary butyl formate and peroxides wherein the feedstock is continuously brought into contact with a bed of a catalyst consisting essentially of sulfuric acid impregnated alumina under reaction conditions including a temperature of about 150° to about 400° C. and a pressure of about 0 to about 3000 psig. at the rate of about 0.5 to about 10 g of feedstock per hour per cc of catalyst, to form a reaction product substantially completely free from tertiary butyl formate and peroxides.

4 Claims, No Drawings

PREPARATION OF ISOBUTYLENE

BACKGROUND OF THE INVENTION

1. Field of the Invention

This invention relates to a method for the continuous preparation of isobutylene substantially free from tertiary butyl formate and peroxides from a tertiary butyl alcohol (TBA) feedstock contaminated with tertiary butyl formate, peroxides and ketones wherein the contaminated tertiary butyl alcohol feedstock is continuously charged to a reactor and contacted therein with a bed of catalyst consisting essentially of sulfuric acid impregnated alumina under reaction conditions including a temperature of about 150° to about 400° C., a pressure of about 0 to about 3000 psig. and a feed rate of about 0.5 to about 10 g of feed per feedstock per hour per cc of catalyst to form a reaction product substantially completely free from tertiary butyl formate.

2. Prior Art

It is known to react isobutane with oxygen, either thermally or catalytically, to form a peroxidation reaction product wherein the principal peroxide that is formed is tertiary butyl hydroperoxide. It is also known to thermally or catalytically decompose the tertiary butyl hydroperoxide to form tertiary butyl alcohol.

Thus, it is known that isobutane can be oxidized with molecular oxygen to form a corresponding tertiary butyl hydroperoxide and by-products and that the reaction can be promoted, for example, with an oxidation catalyst (see Johnson U.S. Pat. No. 3,825,605 and Worrell U.S. Pat. No. 4,296,263).

A process for the manufacture of substituted epoxides from alpha olefins such as propylene is disclosed in Kollar U.S. Pat. No. 3,351,653 which teaches that an organic peroxide compound such as tertiary butyl hydroperoxide can be reacted with an olefinically unsaturated compound such as propylene in the presence of a soluble molybdenum catalyst. The products of the reaction are propylene oxide and tertiary butyl alcohol.

Thus, tertiary butyl alcohol can be prepared either by the direct thermal or catalytic reduction of tertiary butyl hydroperoxide to tertiary butyl alcohol or by the catalytic reaction of propylene with tertiary butyl hydroperoxide to provide propylene oxide and tertiary butyl alcohol.

When isobutane is reacted with oxygen, a wide variety of oxidation by-products are also formed in small amounts including, for example, methyl formate, acetone, 2-butanone, isobutylene oxide, isobutyraldehyde, methanol, methyl tertiary butyl peroxide, isopropyl alcohol, tertiary butyl alcohol, ditertiary butyl peroxide, tertiary isopropyl peroxide and tertiary butyl formate.

These oxidation by-products will remain with the tertiary butyl alcohol product that is formed by the direct or indirect decomposition of the tertiary butyl hydroperoxide.

Sanderson et al. U.S. Pat. No. 4,873,380 discloses, for example, that the peroxide-type contaminants can be removed from tertiary butyl alcohol by bringing the contaminated tertiary butyl alcohol into contact with a nickel, copper, chromium and barium catalyst. The resultant tertiary butyl alcohol product is substantially free from the other peroxide contaminants.

Processes for the preparation of tertiary butyl alcohol from tertiary butyl hydroperoxide are disclosed, for example, in a series of Sanderson et al. patents (U.S. Pat. Nos. 4,910,349; 4,912,266; 4,912,267; 4,922,033; 4,922,034; 4,922,035; 4,992,036; 4,992,602; and 5,025,113).

It is also known that tertiary butyl alcohol can be dehydrated to form isobutylene. For example, Grane et al. U.S. Pat. No. 3,665,048 discloses a process for obtaining essentially pure isobutylene by the controlled dehydration of tertiary butyl alcohol in the presence of an aluminum oxide catalyst.

European Patent Application 0255948, filed May 8, 1987, by Mitsubishi Rayon Company, Ltd., in the names of Kazutaka Inoue et al. discloses a process for the production of isobutylene by the dehydration of tertiary butyl alcohol in gas phase over a fixed bed-type of silica alumina catalyst in the presence of added nonreactive gas to inhibit isobutylene polymer formation.

The dehydration of tertiary butyl alcohol to isobutylene is also disclosed in an article by Heath et al. ("Acid Resin Catalysis: The Dehydration of t-butyl Alcohol", *AICHE Journal* (Vol. 18, No. 2, March 1972, pp. 321-326)).

The prior art references directed to the dehydration of tertiary butyl alcohol to form isobutylene are not directed to the problem that is involved by the presence of tertiary butyl formate as a contaminant which is the case when the tertiary butyl alcohol is formed directly or indirectly from tertiary butyl hydroperoxide. Thus, the tertiary butyl formate will normally be present in the tertiary butyl alcohol feedstock and will also be present in the isobutylene reaction product as a contaminant. The prior art processes use essentially pure tertiary butyl alcohol as a product.

If the isobutylene is reacted with methanol to provide methyl tertiary butyl ether, a motor fuel additive, the tertiary butyl formate and peroxides will be present in the methyl tertiary butyl alcohol motor fuel additive and would be very deleterious insofar as the octane enhancing qualities of the methyl tertiary butyl ether are concerned. Therefore, removal of the tertiary butyl formate and peroxides is very important when tertiary butyl alcohol is to be dehydrated to form isobutylene for use in the preparation of methyl tertiary butyl ether.

SUMMARY OF THE INVENTION

The feedstock of the present invention comprises a tertiary butyl alcohol contaminated with tertiary butyl formate, such as a tertiary butyl alcohol product obtained by the thermal or catalytic decomposition of tertiary butyl hydroperoxide.

The catalyst to be used in accordance with the present invention is a sulfuric acid impregnated alumina catalyst such as a Porocel ® alumina impregnated with from about 0.5 to about 5 wt. % of sulfuric acid. Activated bauxite impregnated with 0.5 to 5 wt. % of sulfuric acid is an example of another sulfuric acid impregnated alumina catalyst.

The process of the present invention is preferably conducted on a continuous basis using a fixed bed of the sulfuric acid impregnated alumina catalyst.

Thus, in accordance with the present invention, a tertiary butyl alcohol (TBA) feedstock contaminated with tertiary butyl formate and peroxides is charged to a reactor containing a fixed bed of sulfuric acid impregnated alumina (e.g., Porocel ® alumina). Suitably, the tertiary butyl formates contaminated tertiary butyl alcohol is charged to the reactor at the rate of about 0.5 to about 5 g of tertiary butyl alcohol feedstock per hour per cc of catalyst and, more preferably, at the rate of about 0.5 to about 3 g of contaminated tertiary butyl alcohol feedstock per cc of catalyst per hour.

Reaction conditions are established in the reactor including suitably a temperature of about 150° to about 400° C. and, more preferably, from about 170° to about 306° C. and a pressure of about 0 to about 3000 psig., such as a pressure of about 0 to about 1,500 psig.

It has been discovered in accordance with the present invention that when tertiary butyl alcohol is dehydrated to isobutylene over the sulfuric acid impregnated alumina, a surprising and unexpected result is obtained in that the tertiary butyl formate and peroxides are substantially completely converted to decomposition products so that the isobutylene that is recovered from the reactor is substantially completely free from tertiary butyl formate and peroxides, and no significant amount of aligomeric isobutylene product is formed.

The invention will be further illustrated by the following specific examples which are given by way of illustration and not as limitations on the scope of this invention.

EXAMPLES

Examples 1-6

A 300 cc electrically heated, stainless steel tubular down-flow reactor which had an inside diameter of 1 inch was used. Crude TBA feed was pumped into the top of the reactor at WHSV of 1.0 g/hr-cc catalyst and atmospheric pressure. The products were analyzed by gas chromatograph. Engelhard's sulfuric acid on R. I. Porocel ® alumina, sulfuric acid on H. A. Porocel ® alumina and activated Baurite ® were examined and the results are listed in Table I.

TABLE I

Dehydration of TBA

| Example | Catalyst | Temp (°C.) | TBA (%) | TBF (%) | DTBP (%) | Isobutylene Selec. (%) |
|---|---|---|---|---|---|---|
| Feed | | | 98.9 | 0.432 | 0.057 | — |
| 1 (6678-26-1) | None | 200 | 95.4 | 0.410 | 0.056 | — |
| 2 (6678-26-2) | None | 220 | 94.8 | 0.400 | 0.039 | — |
| 3 (6678-16-3) | Porocel* | 200 | <1 | 0.003 | — | 97 |
| 4 (6678-16-4) | Porocel* | 220 | <1 | — | — | 96 |
| 5 (6678-25-2) | Activated Baurite ® | 200 | <1 | — | — | 99 |
| 6 (6678-24-2) | Porocel* | 200 | <1 | — | — | 99 |

*Sulfuric acid on R. I. Porocel 20/60

The porocel alumina that is treated with sulfuric acid will be composed primarily of alumina and other metal oxides in minor amounts such as iron oxide, titania and silica. However, the alumina will constitute about 70% to 90% of the support.

Example 7 (6678-45)

A 300 cc electrically heated, stainless steel tubular up-flow reactor which had an inside diameter of 1 inch was used. Crude TBA feed was pumped into the bottom of the reactor at WHSV of 1.0 g/hr-cc catalyst, 800 psig, and 230° C. Engelhard's surfuric acid on H. A. Porocel 20/60 was used. The reaction was run for 200 hours. About 95% of TBA conversion with 98% of isobutylene selectivity was obtained. Both TBF and DTBP was decomposed effectively. No catalyst deactivation was noted during the run.

Having thus described our invention, what is claimed is:

1. A method for the continuous preparation of isobutylene substantially free from tertiary butyl formate from a tertiary butyl alcohol feedstock contaminated with methyl formate which comprises the steps of:

continuously charging a tertiary butyl alcohol feedstock contaminated with tertiary butyl formate to a reactor and contacting it therein with a bed of a catalyst consisting essentially of sulfuric acid impregnated alumina under reaction conditions including a temperature of about 150° to about 400° C. and a pressure of about 0 to about 3000 psig. at the rate of about 0.5 to about 10 g of feedstock per hour per cc of catalyst, to form a reaction product substantially completely free from tertiary butyl formate, withdrawing the reaction product from said reactor, and recovering a tertiary butyl formate-free isobutylene product from the said reaction product.

2. A method as in claim 1 wherein the catalyst consists essentially of an alumina support impregnated with about 0.5 to about 5 wt. % of sulfuric acid, based on the weight of the support.

3. A method as in claim 2 wherein the catalyst support is a porous support consisting essentially of about 70 to about 90 wt. % of alumina, the balance of the support consisting of metal oxides.

4. A method as in claim 1 wherein the tertiary butyl alcohol feedstock is brought into contact with the sulfuric acid impregnated catalyst under reaction conditions including a temperature of about 170° to about 300° C. and a pressure of about 0 to about 1,500 psig. at the rate of about 0.5 to about 3.0 g of feedstock per hour per cc of catalyst.

* * * * *